(12) United States Patent
Chen et al.

(10) Patent No.: US 9,961,840 B2
(45) Date of Patent: May 8, 2018

(54) METHOD AND DEVICE FOR SUPPLYING HEAT ENERGY AND CARBON DIOXIDE FROM EXHAUST GAS FOR VEGETABLE AND/OR ALGAE PRODUCTION

(71) Applicant: Sunshine Kaidi New Energy Group Co., Ltd., Wuhan (CN)

(72) Inventors: Yilong Chen, Wuhan (CN); Shuchuan Hu, Wuhan (CN); Yanfeng Zhang, Wuhan (CN)

(73) Assignee: Sunshine Kaidi New England Group Co., Ltd., Wuhan (CN)

( * ) Notice: Subject to any disclaimer, the term of this patent is extended or adjusted under 35 U.S.C. 154(b) by 73 days.

(21) Appl. No.: 14/040,678

(22) Filed: Sep. 28, 2013

(65) Prior Publication Data
US 2014/0026473 A1    Jan. 30, 2014

Related U.S. Application Data

(63) Continuation-in-part of application No. PCT/CN2012/073414, filed on Mar. 31, 2012.

(30) Foreign Application Priority Data

Apr. 2, 2011    (CN) .......................... 2011 1 0083211

(51) Int. Cl.
*A01G 7/02*    (2006.01)
*A01G 33/00*    (2006.01)
(Continued)

(52) U.S. Cl.
CPC .............. *A01G 7/02* (2013.01); *A01G 33/00* (2013.01); *C12N 1/12* (2013.01); *F28F 1/00* (2013.01); *Y02P 60/247* (2015.11)

(58) Field of Classification Search
CPC ... A01G 7/00; A01G 7/02; A01G 9/18; A01G 9/14; A01G 33/00
(Continued)

(56) References Cited

U.S. PATENT DOCUMENTS 3,999,329 A * 12/1976 Brais ...................... A01G 9/246
261/17
4,073,089 A * 2/1978 Maginnes ................ A01G 9/18
47/17
(Continued)

FOREIGN PATENT DOCUMENTS

EP    2873316 A1 * 5/2015

*Primary Examiner* — Lisa L Tsang
(74) *Attorney, Agent, or Firm* — Matthias Scholl, PC; Matthias Scholl

(57) ABSTRACT

A method for supplying heat energy and carbon dioxide for vegetables and/or algae production using exhaust gas. The method includes: 1) introducing the exhaust gas to a primary heat exchanger to conduct a first indirect heat exchange between the exhaust gas and air from a vegetable greenhouse and/or an algae culturing house, thereby providing hot air for the vegetable greenhouse and/or the algae culturing house; 2) introducing part of the exhaust gas after the first indirect heat exchange to a secondary heat exchanger to conduct a second indirect heat exchange between the exhaust gas and outdoor air; 3) introducing the exhaust gas to a $CO_2$ pressure swing adsorption device, separating and pumping carbon dioxide to a carbon dioxide storage tank for storage; and 4) supplying the carbon dioxide to the vegetable greenhouse and/or a carbon-absorption tank of the algae culturing house.

2 Claims, 4 Drawing Sheets

(51) Int. Cl.
*C12N 1/12* (2006.01)
*F28F 1/00* (2006.01)

(58) Field of Classification Search
USPC ..... 47/1.01 R, 1.4, 58.1 R, 58.1 SE, 58.1 FV
See application file for complete search history.

(56) References Cited

U.S. PATENT DOCUMENTS

| | | | | |
|---|---|---|---|---|
| 4,265,300 | A * | 5/1981 | Kurimoto | A01G 9/246 165/47 |
| 5,659,977 | A * | 8/1997 | Jensen | A01G 33/00 34/547 |
| 5,682,709 | A * | 11/1997 | Erickson | A01G 7/02 47/1.4 |
| 6,205,704 | B1 * | 3/2001 | Schmitz | A01G 9/18 47/17 |
| 8,969,067 | B2 * | 3/2015 | Martin | C12M 21/02 435/257.2 |
| 2005/0252215 | A1 * | 11/2005 | Beaumont | A01G 7/02 60/753 |
| 2008/0009055 | A1 * | 1/2008 | Lewnard | B01D 53/84 435/262 |
| 2011/0291425 | A1 * | 12/2011 | Juranitch | C01B 3/56 290/1 R |
| 2012/0295336 | A1 * | 11/2012 | Hazlebeck | C12N 1/12 435/257.1 |

* cited by examiner

METHOD AND DEVICE FOR SUPPLYING HEAT ENERGY AND CARBON DIOXIDE FROM EXHAUST GAS FOR VEGETABLE AND/OR ALGAE PRODUCTION

CROSS-REFERENCE TO RELATED APPLICATIONS

This application is a continuation-in-part of International Patent Application No. PCT/CN2012/073414 with an international filing date of Mar. 31, 2012, designating the United States, now pending, and further claims priority benefits to Chinese Patent Application No. 201110083211.2 filed Apr. 2, 2011. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

Field of the Invention

The invention relates to recycling and utilization of exhaust gas from a biomass power plant, and more particularly to a method and a device for supplying heat energy and carbon dioxide for vegetables and/or algae using exhaust gas from an electric power plant.

Description of the Related Art

Exhaust gas from the combustion of biomass contains a large amount of water vapor, 12-20% of carbon dioxide, and a small amount of carbon monoxide, sulfur dioxide, nitrogen oxides and dust. The temperature of the exhaust gas is approximately between 110 and 140° C., so that the exhaust gas also contains a large amount of heat energy. However, this part of heat energy carried by the exhaust gas is wasted accompanying with the direct discharge of the exhaust gas.

To ensure the supply of vegetables in winter, vegetable greenhouses are widely used. However, heating systems of most of the vegetable greenhouses use coal as the fuel, the combustion of which has low heat efficiency. The coal fuel combustion results in serious waste and environmental pollution, and gas poisoning accident often happens. Furthermore, as the heat supply is not sufficient, the vegetables in winter grow slowly, thereby resulting in high price of the vegetables.

A typical method to solve problems of the vegetable production and the heat supply in winter includes introducing exhaust gas from the biomass power plant directly into the vegetable greenhouse to accelerate the growth of the vegetables by the exhaust heat and carbon dioxide. However, the exhaust gas contains a small amount of poisonous carbon monoxide, which inhibits the growth of the vegetables.

SUMMARY OF THE INVENTION

In view of the above-described problems, it is one objective of the invention to provide a method and a device for supplying heat energy and carbon dioxide for vegetables and/or algae using exhaust gas from an electric power plant. The method and the device target at comprehensively utilizing the exhaust gas from a coal-fired power plant or biomass boiler to decrease the energy waste and the environmental pollution resulting from the direct discharge of the exhaust gas, and providing heat energy and carbon dioxide to meet the required temperature and the appropriate concentration of carbon dioxide for the growth of the vegetables and/or algae, thereby facilitating the growth of the vegetables and/or the algae, shortening the growth cycle, improving the yield in each area unit, lowering the production cost, increasing the income of the farmer, and solving the problem of short supply of the vegetables.

To achieve the above objective, in accordance with one embodiment of the invention, there is provided a method for supplying heat energy and carbon dioxide for vegetables and/or algae using exhaust gas from an electric power plant, the method comprising the following steps:

1) introducing the exhaust gas from the electric power plant to a primary heat exchanger via an exhaust gas supply pipeline to conduct a first indirect heat exchange between the exhaust gas and air from a heat supply system of a vegetable greenhouse and/or an algae culturing house whereby providing hot air for the vegetable greenhouse and/or the algae culturing house;

2) introducing part of the exhaust gas after the first indirect heat exchange in the first heat exchanger to a secondary heat exchanger via an exhaust gas transport pipeline to conduct a second indirect heat exchange between the exhaust gas and outdoor air whereby further reducing a temperature of the exhaust gas for facilitating adsorption of carbon dioxide;

3) introducing the exhaust gas after the second indirect heat exchange in the second heat exchanger to a $CO_2$ pressure swing adsorption device, separating carbon dioxide from the exhaust gas and pumping the carbon dioxide to a carbon dioxide storage tank for storage; and 4) supplying the carbon dioxide from the carbon dioxide storage tank to the vegetable greenhouse and/or a carbon-absorption tank of the algae culturing house during a growth period of vegetables and/or algae.

In a class of this embodiment, in step 2), the outdoor air is heated by the exhaust gas and is introduced to a tertiary heat exchanger for heat exchange with circulating water of a warm water supply system of the carbon-absorption tank to provide warm water for the carbon-absorption tank. Thus, the exhaust heat of the exhaust gas is fully utilized to provide an appropriate temperature of the water for the growth of the algae.

In a class of this embodiment, in step 1), a temperature of the exhaust gas from the electric power plant is between 110 and 140° C.; a temperature of the exhaust gas after the first indirect heat exchange in the first heat exchanger is between 80 and 90° C.; and a temperature of the hot air provided for the vegetable greenhouse and/or algae culturing house is between 40 and 50° C.

In a class of this embodiment, in step 2), a temperature of the exhaust gas after the second indirect heat exchange in the second heat exchanger is between 50 and 60° C.; a temperature of the outdoor air heated by the exhaust gas is between 40 and 50° C.; and a water temperature of the carbon-absorption tank is between 25 and 35° C.

In a class of this embodiment, in step 4), the carbon dioxide is supplied once every day at sunny period. A concentration of the carbon dioxide in the vegetable greenhouse is controlled at between 600 and 1200 ppm. The vegetable greenhouse is sealed for between 1.5 and 2.0 hours for receiving the carbon dioxide, and then a ventilating opening thereof is opened for removal of humidity. Thus, an appropriate concentration of the carbon dioxide is provided for facilitating the growth of the vegetables so that the yield of the vegetables in each area unit is largely increased.

In accordance with another embodiment of the invention, there provided a device for supplying heat energy and carbon dioxide for vegetables and/or algae, the device comprising: a draft fan, the exhaust gas supply pipeline connected to the draft fan, the primary heat exchanger, the exhaust gas transport pipeline connected to a chimney, the secondary heat exchanger, the $CO_2$ pressure swing adsorption device, and the carbon dioxide storage tank.

The primary heat exchanger employs a shell-and-tube heat exchanger comprising a gas inlet pipeline, a gas outlet pipeline, an air inlet pipeline, and an air outlet pipeline. The gas inlet pipeline is connected to the exhaust gas supply pipeline via a first pressure blower. The gas outlet pipeline is connected to the exhaust gas transport pipeline. The air inlet pipeline is connected to an air recycling pipeline of the heat supply system of the vegetable greenhouse and/or the algae culturing house via a second pressure blower. The air outlet pipeline is connected to an air outlet pipeline of the heat supply system of the vegetable greenhouse and/or the algae culturing house.

The secondary heat exchanger employs a heat pipe exchanger comprising a cold air input end, an exhaust gas input end, and an exhaust gas output end. The cold air input end communicates with the outdoor air via a circulating pump. The exhaust gas input end is connected to the exhaust gas transport pipeline via a compressor. The exhaust gas output end is connected to an input end of the $CO_2$ pressure swing adsorption device. An output end of the $CO_2$ pressure swing adsorption device is connected to the carbon dioxide storage tank via a vacuum pump. The carbon dioxide storage tank is connected to the vegetable greenhouse and/or the carbon-absorption tank of the algae culturing house via a $CO_2$ transport pipe and a control valve disposed thereon.

In a class of this embodiment, the device further comprises a tertiary heat exchanger. The tertiary heat exchanger employs a gas-liquid heat exchanger comprising an air inlet, an air outlet, a warm water output end, and a warm water return end. The air inlet is connected to a hot air output end of the heat pipe exchanger via an air transport pipeline, and the air outlet communicates with the air via an exhaust pipeline. The warm water output end is connected to a water inlet of the carbon-absorption tank via a circulating water pump, and the warm water return end is connected to a water outlet of the carbon-absorption tank via a magnetic valve.

The heat energy carried by the exhaust gas is extracted by the indirect heat exchange between the exhaust gas and the air, and the carbon dioxide carried by the exhaust gas is extracted using the $CO_2$ pressure swing adsorption device.

Advantages of the invention are summarized as follows:
   First, the indirect heat exchange is used for supplying heat for the vegetable greenhouse and/or the algae culturing house. Not only does the waste heat in the exhaust gas is fully utilized to decreased the operation cost of the heat supply system, but also the consumption of the coal fuel for supplying heat is effectively lowered thereby realizing the energy conservation. The indirect heat exchange is particularly applicable to the biomass power plant distributed close to the agriculture production area.
   Second, the carbon dioxide carried by the exhaust gas is extracted and supplied to the vegetable greenhouse and/or the carbon-absorption tank of the algae culturing house, so that a small amount of the poisonous component in the exhaust gas is prevented from polluting the vegetables and/or the algae, the growth of the vegetables and/or the algae is greatly facilitated, and the problem of the shortage of the winter vegetables is solved.
   Finally, after the waste heat and the carbon dioxide in the exhaust gas are extracted by the vegetables and other biomass, the energy waste and the environmental pollution resulted from direct discharge of the exhaust gas is effectively prevented, and the greenhouse effect is alleviated. Besides, the biomass produced from the vegetable greenhouse and the algae culturing house is then used as the fuel of the power plant so that a beneficial cycle is formed.

BRIEF DESCRIPTION OF THE DRAWINGS

The invention is described hereinbelow with reference to the accompanying drawings, in which.

DETAILED DESCRIPTION OF THE EMBODIMENTS

The invention is further described hereinbelow combined with the drawings.

Figure 1:
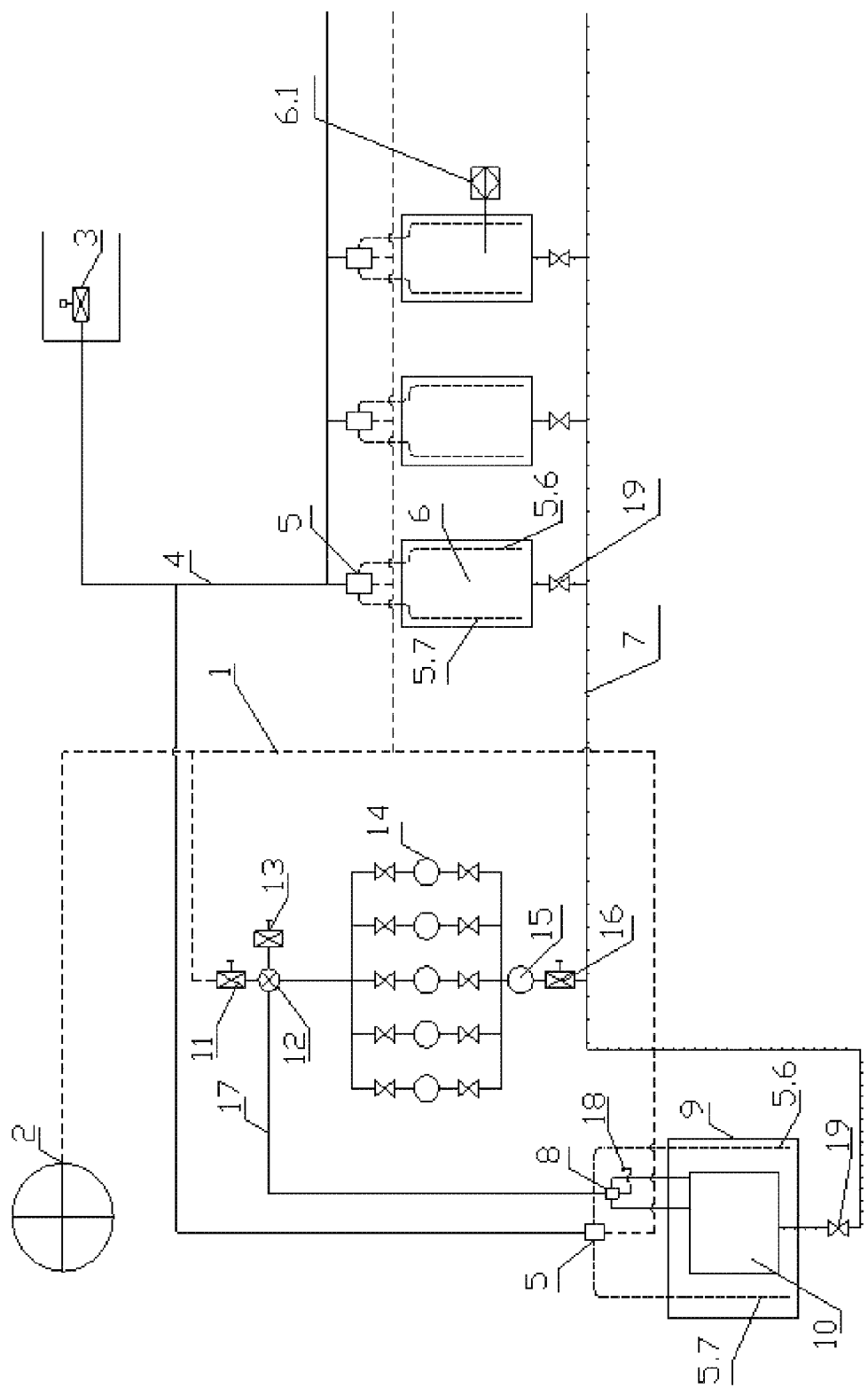
FIG. 1 is a structure diagram of a device for supplying heat energy and carbon dioxide for vegetables and/or algae.
Figure 2:
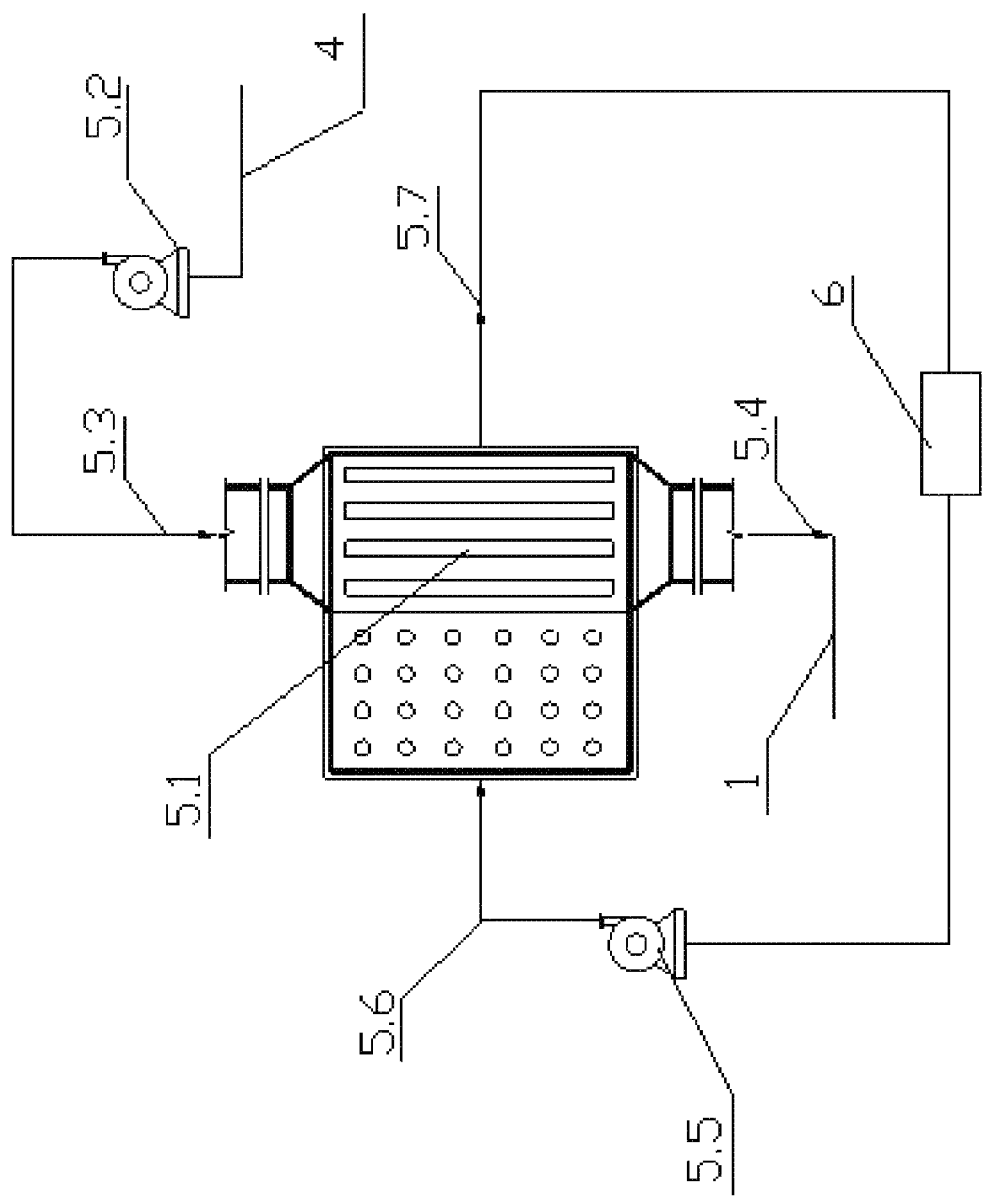
FIG. 2 is a structure diagram of a primary heat exchanger in FIG. 1.
Figure 3:
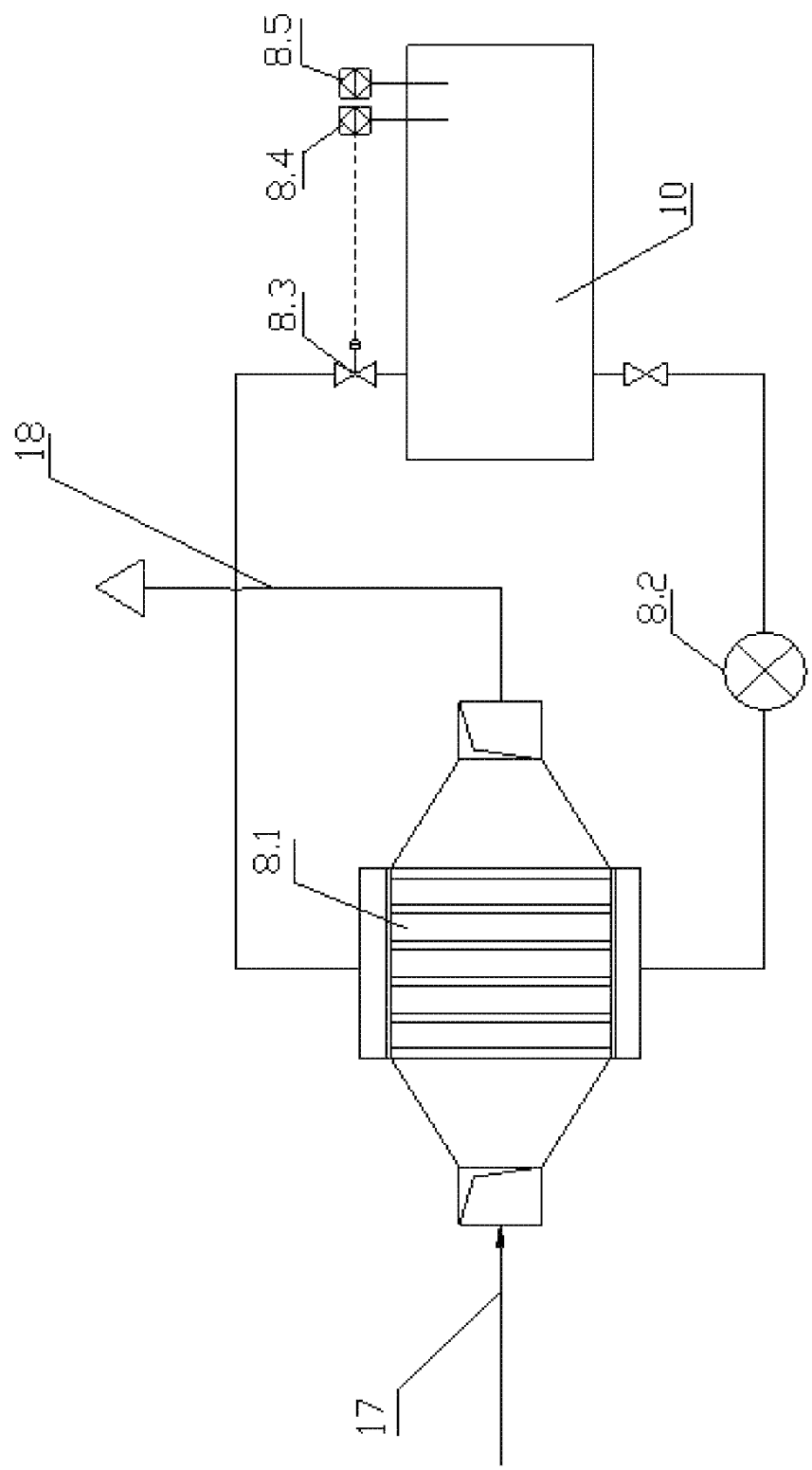
FIG. 3 is a structure diagram of a tertiary heat exchanger in FIG. 1.
Figure 4:
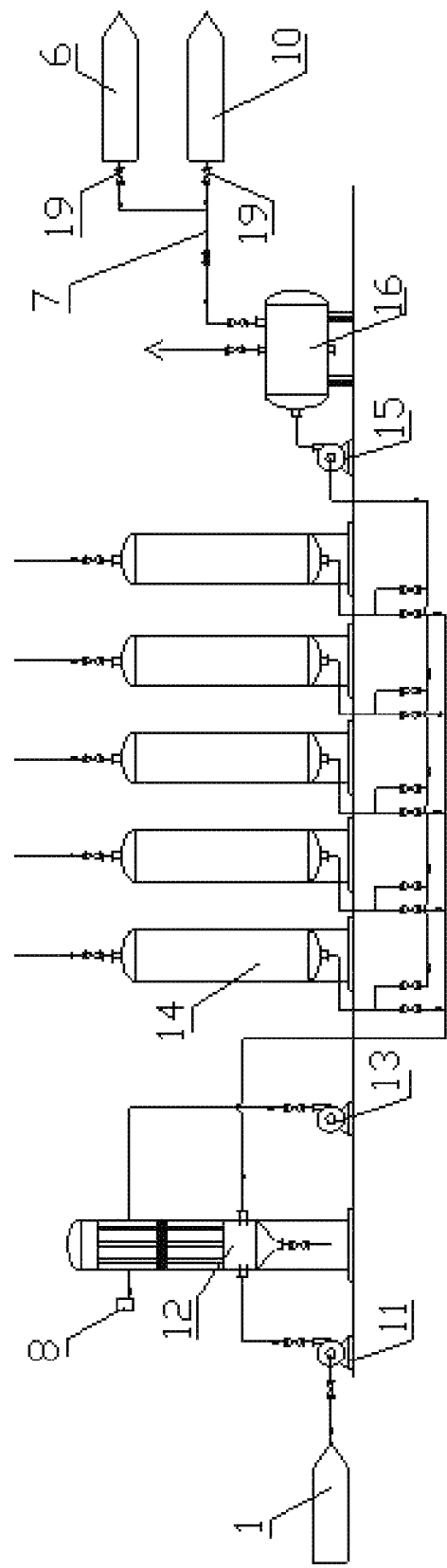
FIG. 4 is a structure diagram of a $CO_2$ pressure swing adsorption device in FIG. 1.

As shown in FIGS. 1-4, a device for supplying heat energy and carbon dioxide for vegetables and/or algae comprises: a draft fan 3 and an exhaust gas supply pipeline 4 connected to the draft fan 3 for extracting the exhaust gas from the boiler of the biomass power plant; an exhaust gas transport pipeline 1 connected to a chimney 2 for discharging the superfluous exhaust gas after the heat exchange treatment; a primary heat exchanger 5, a secondary heat exchanger 12, and a tertiary heat exchanger 8 for achieving the indirect heat exchange between the exhaust gas with the clean air and the water for providing heat and warm water for the vegetable greenhouse 6 and the algae culturing house 9; and a $CO_2$ pressure swing adsorption device 14 and a carbon dioxide storage tank 16. The $CO_2$ pressure swing adsorption device 14 employs a silica gel or an activated carbon as an adsorbent. Carbon dioxide is extracted by the $CO_2$ pressure swing adsorption device 14 by a pressure difference to be replenished to a vegetable greenhouse 6 or a carbon-absorption tank 10 of an algae culturing house 9.

The primary heat exchanger 5 employs a shell-and-tube heat exchanger 5.1 comprising a gas inlet pipeline 5.3, a gas outlet pipeline 5.4, an air inlet pipeline 5.6, and an air outlet pipeline 5.7. The gas inlet pipeline 5.3 is connected to the exhaust gas supply pipeline 4 via a first pressure blower 5.2. The gas outlet pipeline 5.4 is connected to the exhaust gas transport pipeline 1. The air inlet pipeline 5.6 is connected to an air recycling pipeline of the heat supply system of the vegetable greenhouse and/or the algae culturing house via a second pressure blower 5.5. The air outlet pipeline 5.7 is connected to an air outlet pipeline of the heat supply system of the vegetable greenhouse and/or the algae culturing house. Thus, the air in the vegetable greenhouse and/or the algae culturing house absorbs heat energy from the exhaust gas by the shell-and-tube heat exchanger 5.1 for supplying heat energy to the vegetables or the algae.

The secondary heat exchanger 12 employs a heat pipe exchanger comprising a cold air input end, an exhaust gas input end, and an exhaust gas output end. The cold air input end communicates with the outdoor air via a circulating pump 13. The exhaust gas input end is connected to a branch of the exhaust gas transport pipeline 1 via a compressor 11 for extracting one part of the exhaust gas after the treatment of the primary heat exchanger 5 and cooling the exhaust gas to an appropriate temperature for the $CO_2$ absorption. The exhaust gas output end is connected to an input end of the $CO_2$ pressure swing adsorption device 14. An output end of the $CO_2$ pressure swing adsorption device 14 is connected to the carbon dioxide storage tank 16 via a vacuum pump 15. The carbon dioxide storage tank 16 is connected to the vegetable greenhouse and/or the carbon-absorption tank 10 of the algae culturing house via a $CO_2$ transport pipe 7 and a control valve 19 disposed thereon for replenishing carbon dioxide to the vegetables or the algae. A $CO_2$ concentration detector 6.1 is arranged inside the vegetable greenhouse for automatically controlling an opening or close of the control valve 19.

The tertiary heat exchanger 8 employs a conventional gas-liquid heat exchanger 8.1 comprising an air inlet, an air outlet, a warm water output end, and a warm water return end. The air inlet is connected to a hot air output end of the heat pipe exchanger via an air transport pipeline 17, and the air outlet communicates with the air via an exhaust pipeline 18. The warm water output end is connected to a water inlet of the carbon-absorption tank 10 via a circulating water pump 8.2, and the warm water return end is connected to a water outlet of the carbon-absorption tank 10 via a magnetic valve 8.3. So that a warm water circulating loop is formed to provide constant warm water to the algae in the carbon-absorption tank 10. The carbon-absorption tank 10 is provided with a temperature sensor 8.4 and a water level sensor 8.5 for automatic opening or closing of the magnetic valve 8.3.

Workflow of the device for supplying heat energy and carbon dioxide for vegetables and/or algae is as follows:

1) exhaust gas having a temperature of 110-140° C. was discharged from the power plant and was extracted by the draft fan 3 to the shell-and-tube heat exchanger 5.1 via the exhaust gas supply pipeline 4 to conduct a first indirect heat exchange with the air from the heat supply system of the vegetable greenhouse 6 and the algae culturing house 9. The air was heated to a temperature of 40-50° C. and was directly transported to the vegetable greenhouse 6 and the algae culturing house 9 for providing heat for the vegetables and the algae. The heat supply system was adjusted to control the vegetable green house at a temperature of 20-28° C. in daytime and a temperature of 14-18° C. at night to meet the requirement of fast growth of the vegetables.

2) A temperature of the exhaust gas after the heat exchange by the shell-and-tube heat exchanger 5.1 was 80-90° C. One part of the exhaust gas was discharged from the chimney 2 through the exhaust gas transport pipeline 1. The other part of the exhaust gas was transported to the heat pipe exchanger 12 under the action of the compressor 11 through one branch of the exhaust gas transport pipeline 1 for conducting a second heat exchange with the outdoor air from the circulating pump 13. The outdoor air was heated to a temperature of 40-50° C.

3) The exhaust gas after the treatment by the heat pipe exchanger 12 had a temperature of 50-60° C. and was transported to the $CO_2$ pressure swing adsorption device 14. The $CO_2$ pressure swing adsorption device 14 used the silica gel or the activated carbon as the absorbent. Carbon dioxide was extracted by the intermittent pressure variation and was transported to the carbon dioxide storage tank 16 for storage by the vacuum pump 15.

4) The outdoor air after being heated by the heat pipe exchanger 12 was transported through the air transport pipeline 17 to a gas-liquid indirect heat exchanger 8.1 for heat exchange with the circulating water of the warm water supply system of the carbon-absorption tank 10. The water temperature of the carbon-absorption tank 10 was maintained at 25-35° C. for facilitating the growth of the algae. The temperature sensor 8.4 and the water level sensor 8.5 were used to monitor the water temperature and the water level in the carbon-absorption tank 10. When the water temperature reached 35° C. and the water level reached a preset level, the magnetic valve 8.3 arranged on the circulating water pipeline of the carbon-absorption tank 10 was closed, and the gas-liquid indirect heat exchanger 8.1 was stopped from operation. When the water temperature was lowered to 25° C., the magnetic valve 8.3 opened and the gas-liquid indirect heat exchanger 8.1 was started to operation again.

5) During the growth cycle of the vegetables and the algae, the carbon dioxide in the $CO_2$ storage tank was replenished to the vegetable greenhouse 6 and the carbon-absorption tank 10 of the algae culturing house 9 according to the demand. For the vegetable greenhouse 6, the carbon dioxide was replenished once in sunny period every day. The $CO_2$ concentration detector 6.1 was used to real time monitor the $CO_2$ concentration in the vegetable greenhouse 6, and the $CO_2$ concentration therein was controlled within a range of 800-1000 ppm by automatic opening or close of the control valve 19. After the vegetable greenhouse was closed for 1.5-2.0 h, ventilating opening was opened to remove the humidity. From the cultivation of a small batch of vegetables such as cucumber and celery, it was known that by utilizing the heat energy and the carbon dioxide from the exhaust gas of the biomass power plant, the yield per unit area of the cucumber and the celery were improved by 26.6% and 39.9%, respectively.

The invention claimed is:

1. A method for supplying heat energy and carbon dioxide for vegetables and/or algae cultivated for consumption using exhaust gas, the method comprising the following steps:

1) introducing an exhaust gas from an electric power plant to a first heat exchanger via an exhaust gas supply pipeline to conduct a first indirect heat exchange between the exhaust gas and a flow of air, said exhaust gas having a temperature of between 110 and 140° C., and then sending the flow of air after the first indirect heat exchange, said air having a temperature of between 40 and 50° C., to a vegetable greenhouse and/or an algae culturing house via a heat supply system, thereby providing hot air for the vegetable greenhouse and/or the algae culturing house,
wherein the flow of air that is sent to the vegetable greenhouse and/or the algae culturing house:
(a) does not comprise the exhaust gas and
(b) directly contacts plants and/or algae in the vegetable greenhouse and/or the algae culturing house;

2) introducing part of the exhaust gas after the first indirect heat exchange in the first heat exchanger to a secondary heat exchanger via an exhaust gas transport pipeline to conduct a second indirect heat exchange between the exhaust gas and an outdoor air, said part of the exhaust gas after the first indirect heat exchange having a temperature of between 80 and 90° C., wherein the outdoor air is heated by the exhaust gas; introducing the outdoor air heated via the second indirect heat exchange to a tertiary heat exchanger to conduct an air-water heat exchange with circulating water in a warm water supply system, and sending the circulating water after the air-water heat exchange to a carbon-absorption tank of the algae culturing house to provide warm water for the carbon-absorption tank; wherein
   a temperature of the exhaust gas after the second indirect heat exchange is between 50 and 60° C.;
   a temperature of the outdoor air after the second indirect heat exchange is between 40 and 50° C.; and
   a water temperature of the circulating water after the air-water heat exchange is between 25 and 35° C.;
3) introducing the exhaust gas after the second indirect heat exchange in the second heat exchanger to a carbon dioxide pressure swing adsorption (PSA) device, separating carbon dioxide from the exhaust gas and pumping the carbon dioxide to a carbon dioxide storage tank for storage; and
4) supplying the carbon dioxide from the carbon dioxide storage tank to the vegetable greenhouse and/or the carbon-absorption tank of the algae culturing house during a growth period of vegetables and/or algae.

2. The method of claim 1, wherein in step 4), when supplying the carbon dioxide to the vegetable greenhouse, the carbon dioxide is supplied once every day at a sunny period; a concentration of carbon dioxide in the vegetable greenhouse is controlled at between 600 and 1200 parts per million (ppm); the vegetable greenhouse is sealed for between 1.5 and 2.0 hours for receiving the carbon dioxide, and then a ventilating opening thereof is opened for removal of humidity.

* * * * *